United States Patent [19]

Yamazaki et al.

[11] Patent Number: 4,554,360
[45] Date of Patent: Nov. 19, 1985

[54] PROCESS FOR CONVERTING AROMATIC COMPOUNDS

[75] Inventors: Yasuo Yamazaki, Machida; Takehiko Suzuki, Tokyo; Isoo Shimizu; Yasuo Matsumura, both of Yokohama, all of Japan

[73] Assignee: Nippon Petrochemicals Company, Limited, Japan

[21] Appl. No.: 594,678

[22] Filed: Mar. 29, 1984

[30] Foreign Application Priority Data

Mar. 29, 1983 [JP] Japan ................................. 58-51584

[51] Int. Cl.$^4$ ........................................... C07D 307/32
[52] U.S. Cl. ....................................... 549/261; 560/8; 560/55; 560/81; 560/64; 560/76; 560/103; 560/102; 560/104; 560/247; 562/499; 548/545; 568/631; 568/647; 568/332; 568/420; 568/928; 568/939; 564/184; 570/182; 570/190; 570/199; 585/436; 585/469
[58] Field of Search ............... 585/436, 469; 570/182, 570/199; 560/104, 102, 103, 81, 55, 647, 8, 64, 76; 568/420, 332, 631, 928, 647, 939; 549/261; 564/184; 562/499; 548/545

[56] References Cited

U.S. PATENT DOCUMENTS 2,878,293  3/1959  Kinzer ................................. 570/182
3,264,355  8/1966  Cannon ............................... 570/182
3,674,884  7/1972  Moritani ............................. 585/436

Primary Examiner—Paul R. Michl
Assistant Examiner—Alex H. Walker
Attorney, Agent, or Firm—Scully, Scott, Murphy & Presser

[57] ABSTRACT

Provided is a process for converting an aromatic compound to prepare an iodoarene, Ar—I, and an aryl compound which is a compound wherein an unsaturated compound is bonded directly to an aryl group, Ar, which process comprises reacting a diaryliodonium salt represented by general formula (I)

$$[Ar\text{—}I^{\oplus}\text{—}Ar]X^{\ominus} \qquad (I)$$

wherein Ar is an aryl group which may be substituted and two Ar's are identical and $X^{\ominus}$ is a counter ion inert to the reaction with the unsaturated compound in a solvent in the presence of a transition metal catalyst and a base or a reducing metal, said reaction being carried out at a temperature not higher than 80° C. and/or by using at least one of the base, the reducing metal and the unsaturated compound in an amount not more than 1.5 times the stoichiometric amount, then separating the iodoarene thus formed, Ar—I, from the reaction mixture, subsequently coupling said iodoarene thus separated with an aromatic compound, ArH, in an oxidizing atmosphere in the presence of $X^{\ominus}$ or an anion ion-exchangeable with $X^{\ominus}$, if needed ion-exchanging the anion with $X^{\ominus}$, to form the diaryl iodonium salt of the above general formula (I), and recycling said diaryl iodonium salt thus formed in said reaction.

8 Claims, No Drawings

4,554,360

PROCESS FOR CONVERTING AROMATIC COMPOUNDS

BACKGROUND OF THE INVENTION

The present invention relates to a process for converting aromatic compounds. More particularly, it is concerned with a process for combining an aromatic compound with a compound containing a double bond in the molecule by addition by the reuse of recycled iodine.

Processes for converting aryl compounds typically exemplified by Friedel-Crafts reaction in which an aromatic compound is reacted with an olefin in the presence of an acid catalyst are needed and important ones in chemical industry. Recently, the conversion processes by the use of a transition metal complex have called attention because of characteristics such as moderate reaction conditions, maintenance of unsaturation of the side chain in the converted aromatic compounds and other advantages. Studies have been made on process for converting aromatic hydrocarbons by the reaction of a aryl halide and a variety of unsaturated compounds with a palladium catalyst. However, there is a need for improvement in the reaction in which the palladium as catalyst is required in an equimolar amount to the amount of the aryl halide. Heek et al. proposed that carboxylic acids and esters thereof are produced by the carbonylation of an aryl halide with carbon monoxide with a catalystic amount of palladium when a base is coexistent (J. Org. Chem., 39, 3318 (1974); J. Org. Chem. 39, 3327 (1974). Since then, important of the reaction has become recognizable. According to this reaction, however, the iodine contained in iodoarene is consumed as an iodide which is a neutral salt when the reaction is completed. Consumption of expensive iodine in the form of a neutral salt is unfavorable from an industrial point of view.

In order that the reaction of iodoarene with a palladium catalyst is commercially valuable, repeated use or recycling of the iodine is essential.

SUMMARY OF THE INVENTION

It is an object of the present invention to recycle expensive iodine by employing a diaryl iodonium salt in place of an iodoarene in the reaction such as Heck' reaction and converting the iodoarene thus formed to a diaryl iodonium salt. Another object is to accomplish the reacting using a diaryl iodonium salt at a low cost.

The present invention relates to a process for converting an aromatic compound to prepare an iodoarene, Ar—I, and an aryl compound which is a compound wherein an unsaturated compound is bonded directly to an aryl group, Ar, which process comprises reacting a diaryl iodonium compound represented by the general formula (I)

$$[Ar-I^{\oplus}-Ar]X^{\ominus} \quad (I)$$

with the unsaturated compound in a solvent in the presense of a transition metal catalyst and a base or a reducing metal.

Wherein: Ar is an aryl group which may be substituted and the second Ar is the same as the first one; $X^{\ominus}$ is a counter ion inert to the reaction.

Particularly, this invention is characterized by carrying out said reaction in order to avoid substantial reaction of the formed iodoarene, Ar—I, further with said unsaturated compound at a temperature not higher than 80° C. and/or by the use of at least one of the base, the reducing metal and the unsaturated compound in an amount not more than 1.5 times the stoichiometric amount, then saparating the iodoarene thus formed Ar—I from the reaction mixture, subsequently coupling said iodoarene thus separated with ArH in an oxidizing atmosphere in the presence of $X^{\ominus}$ or an anion ion-exchangeable with $X^{\ominus}$, if needed ion-exchanging the anion with $X^{\ominus}$, to form the diaryl iodonium salt of the above general formula (I), and recycling said diaryl iodonium salt thus formed in said reaction.

DETAILED DESCRIPTION OF THE INVENTION

The first of the characteristic features of the present invention is the operation under such conditions that an iodoarene is produced simultaneously with the desired addition product (an aryl compound) and the iodoarene will not undergo further reaction to produce a neutral salt. The second characteristic feature is repeated use of the by-produced iodoarene reverted to the iodonium salt by coupling with an aromatic compound in an oxidizing atmosphere.

The first stage reaction which is a reaction between a diaryl iodonium salt and an unsaturated compound will be described below in the form of a reaction between diphenyl iodonium bromide and carbon monoxide in the presence of a palladium catalyst and a base. The reaction scheme is as below.

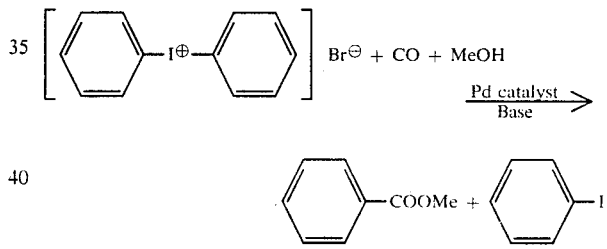

There are produced methyl benzoate and iodobenzene. Bromine which is the counter ion forms a bromide with the base. In this reaction methanol acts also as the solvent.

According to the aforementioned reaction of Heck et al., however, iodine is converted to a neutral salt as a result that by-produced iodobenzene is reacted with carbon monoxide in the presence of a palladium catalyst and a base. It is difficult to recycle the iodine in the form of a neutral salt easily and at a low cost.

It is therefore critical in the first-stage reaction to carry out the operation under such conditions that the iodoarene such as iodobenzene will not undergo further reaction thereby minimizing the loss of iodine. The reaction conditions will be described below in more details.

The diaryl iodonium salt used in the invention is represented by the general formula (I) as described above. The aryl group is a monovalent substituent derived from the aromatic nucleus of a condensed or uncondensed aromatic hydrocarbon by withdrawing one hydrogen atom. Said aromatic hydrocarbon may have any one or more of the substituents that are stable in the presence of a base and is derived from benzene, indane, naphthalene or the like. The two aryl groups Ar of the diaryl iodonium salt are the same.

As examples of the diaryl iodonium salt are mentioned diphenyl iodonium salts represented by the formula below and substituted ones thereof.

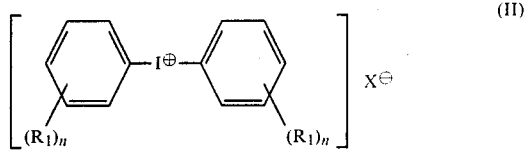

wherein $R_1$ is hydrogen atom, a $C_1$–$C_{12}$ alkyl group, a cycloalkyl group, an aryl group, a halogenoalkyl group, a halogen atom, a carboxyl group, an alkoxycarbonyl group, an alkoxyl group, nitro group or an acylamino group, and n is an integer from 0 to 3 inclusive.

As the alkyl group in the above formula are mentioned $C_1$–$C_{12}$ alkyl groups such as methyl, ethyl, propyl, isopropyl, butyl, t-butyl and isobutyl. Cycloalkyls of $C_6$–$C_{12}$ such as cyclohexyl may be mentioned. The halogenoalkyl group includes lower groups such as trifluoromethyl and the like. The alkoxycarbonyl group includes lower alkoxycarbonyl groups such as methoxycarbonyl, ethoxycarbonyl and propoxycarbonyl. As the acylamino group are mentioned $C_1$–$C_{12}$ acylamino groups such as acetylamino, succinimido and phthalimido. The benzene ring may be substituted with up to three of above substituents.

As examples of the diaryl iodonium salt are mentioned salts of diphenyl iodonium, bis(alkylphenyl)iodonium such as ditolyl iodonium, dicumenyl iodonium, bis(iso-butylphenyl)iodonium and bis(t-butylphenyl)iodonium, bis(cyclohexylphenyl)iodonium, dibiphenylyliodonium, bis(halogenoalkylphenyl)iodonium such as bis(trifluoromethylphenyl)iodonium, bis(halogenophenyl)iodonium such as bis(chlorophenyl)iodonium and bis(bromophenyl)iodonium, bis(carboxylphenyl)iodonium, bis(alkoxyphenyl)iodonium such as bis(methoxyphenyl)iodonium and bis(ethoxyphenyl)iodonium, bis(nitrophenyl)iodonium, bis(acylaminophenyl)iodonium such as bis(acetylaminophenyl)iodonium and the like.

These diaryl iodonium ions form salts with a counter ion $X^\ominus$ as shown in the above-mentioned formulae (I) and (II). Nature of the counter ion $X^\ominus$, however, is not essential for the present invention. Therefore, it may be any of anions that are inert to the reaction. Usually, it is selected depending upon the method by which the iodonium salt is obtained. Bisulfate ion, anions from mineral acids such as chloride ion, bromide ion and iodide ion, and halogenated metal ions such as boron tetrafluoride ion, phosphorus hexafluoride ion, arsenic hexafluoride ion and antimony hexafluoride ion are mentioned. These counter ions can be ion-exchanged each other, and preferable are halogenide such as bromide ion.

Halogenide salts of these diaryl iodoniums can be prepared, for example, by the methods described in U.K. Pat. Nos. 1114950, 1542068 and 1572620 as well as by the method of Beringer et al. described in J. Am. Chem. Soc. 81, 342 (1959). For example, they are prepared from benzene, alkylbenzenes such as toluene, isopropylbenzene, isobutylbenzene and t-butylbenzene, indane, halobenzenes such as chlorobenzene and bromobenzene, benzoic acid, anisole, nitrobenzene, acetanilide and biphenyl. The method will be described by taking as an example a method of preparing a diphenyl iodonium salt from benzene as below.

To a mixture of benzene and potassium iodate ($KIO_3$) in acetic anhydride is dropwise added a mixture of acetic anhydride and concentrated sulfuric acid followed by stirring. To the resulting mixture is added saturated aqueous solution of ammonium chloride to form precipitates, which are separated by filtration and recrystallized to give diphenyl iodonium chloride.

In the first-stage reaction of the invention, which is a reaction between an unsaturated compound and a diaryl iodonium salt, the desired aryl compound is obtained by combining one aryl group of said iodonium salt with the said unsaturated compound.

Among such unsaturated compounds are compounds containing an olefinic double bond. The double bond is combined with the aryl group. The double bond remains as it is with most of the olefinic double bond-containing compounds, but it is not so in all of them. It is necessary that the olefinic double bond is not a double bond of the so-called tetra-substituted type but at least one hydrogen atom on the two carbon atoms constituting the double bond is substituted.

Accordingly, the above-mentioned olefinic double bond-containing compounds are represented by the general formula (III)

wherein $R_2$, $R_3$ and $R_4$ respectively are substituents inert to the present reaction such as hydrogen, a $C_1$–$C_{12}$ alkyl group a $C_6$–$C_{12}$ cycloalkyl group, a lower aryl group, a cyano group, a lower alkoxycarbonyl group or a lower acyl group, and the dotted line represents a bond which may be existing.

Examples of the above-mentioned olefinic double bond-containing compound are aliphatic olefins such as ethylene, propylene and isobutylene, styrenes such as styrene, vinyltoluene, α- or β-methylstyrene and isopropenyltoluene and acrylonitrile as well as α,β-unsaturated carbonyl compounds. The α,β-unsaturated compounds include lower alkyl esters of α,β-unsaturated monocarboxylic acids such as methyl, ethyl and propyl esters of acrylic acid, metacrylic acid, crotonic acid, isocrotonic acid, atropic acid, cinnamic acid and the like. These esters are represented by the following formula:

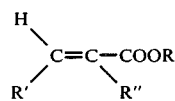

wherein R is a lower alkyl group and R' and R" respectively are H or $C_1$–$C_{12}$ alkyl, aryl or aralkyl group.

Also mentioned are lower alkyl diesters of α,β-unsaturated dicarboxylic acids such as methyl, ethyl and propyl esters of maleic acid, fumaric acid, citraconic acid, methaconic acid and the like. These diesters are represented by the following formula:

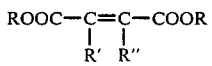

wherein R is a lower alkyl group and R' and R" respectively are a $C_1$–$C_{12}$ alkyl, aryl or aralkyl group.

Anhydrides of α,β-unsaturated dicarboxylic acids such as maleic acid and citraconic acid may be mentioned as the α,β-unsaturated compounds. These anhydrides are represented by the following formula:

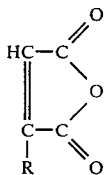

wherein R is H or a $C_1$–$C_{12}$ alkyl, aralkyl or aryl group.

Furthermore, α,β-unsaturated ketones and α,β-unsaturated aldehydes such as methylvinylketone and acrolein represented by the formula below are mentioned as the α,β-unsaturated carbonyl compounds.

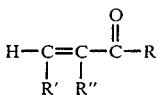

wherein R, R' and R" respectively are H or a $C_1$–$C_{12}$ alkyl, aryl or aralkyl group.

Therefore, the aryl compounds obtained as the object of the invention are represented by the following formula (IV), for which the reaction scheme is also shown as follows:

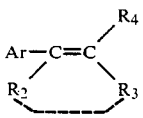 (IV)

Reaction scheme

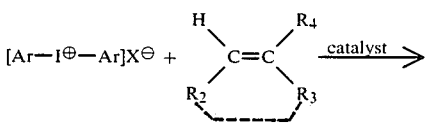

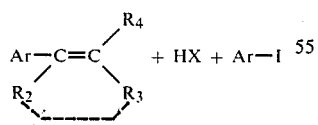

wherein Ar, $R_2$, $R_3$ and $R_4$ are as defined above.

As shown above, reaction of a diphenyl iodonium salt with styrene affords stilben, and with acrylic esters there are produced such aryl compounds as cinnamic esters.

When the unsaturated compound is unsaturated alcohols represented by the formula below such as allyl alcohol or methallyl alcohol, said unsaturated compound is combined with the aryl group without the double bond maintained and the hydroxyl group is simultaneously converted to formyl group.

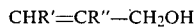

wherein R' and R" respectively are H or a $C_1$–$C_{12}$ alkyl group.

The aryl compound thus obtained is as follows.

wherein Ar, R' and R" are as defined above.

A further example of the aforementioned unsaturated compounds is carbon monoxide. It is necessary in order to carry out the reaction in the above case that water, a lower alcohol such as methanol, ethanol or butanol or an aromatic amine such as aniline is present. As a result of the reaction, a carbonyl group is introduced into the aryl group.

When water or an alcohol represented by R—OH wherein R is H or a lower alkyl group aromatic amine such as aniline represented by φ—$NH_2$ is employed, there is obtained an aryl compound represented by the following formula by the reaction scheme shown as follows:

Reaction scheme

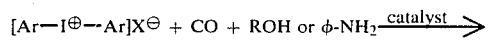

If an excess amount of the alcohol or aniline and the like is employed, it acts also as a solvent.

As shown above, when a diphenyl iodonium salt is reacted with carbon monoxide in the presence of methanol, there is produced methyl benzoate.

If the above-described addition reaction, which is the addition of carbon monoxide in the presence of a base, is carried out in the presence of a reducing metal such as zinc or copper in place of the base, there is produced a diaryl ketone or a diaryl diketone as shown below.

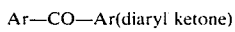

Reaction scheme (Me: monovalent metal, for example)

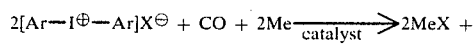

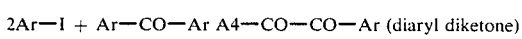

Reaction scheme (Me: monovalent metal, for example)

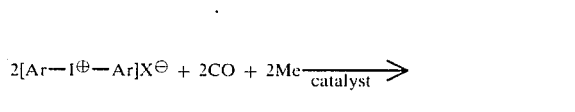

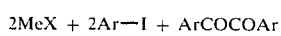

wherein Ar is defined above.

As shown above, when a diphenyl iodonium salt is reacted with in the presence of zinc in place of a base, the aryl compound obtained is benzophenone or bibenzil.

The transition metal catalyst used in the present invention is an element of the Group VIII in the Periodic Table such as, for example, palladium, rhodium, rutenium, platinum, iridium, osmium or nickel. A palladium catalyst including palladium is particularly preferred. The transition metal may be employed as the catalyst in various forms. It may be in any oxidation number or in any form of complex. Palladium, for example, may be employed in metal palladium such as in the form of palladium black, palladium carried on alumina or active carbon, and in multivalent palladium such as in the form of halogenated palladiums including palladium chloride, palladium oxide, or a palladium salt with lower fatty acids such as palladium acetate or in complex such as in the form of bis(dibenzylideneacetone)palladium, bis(acetylacetone)palladium, tetrakis(triphenylphosphine)palladium, bis(triphenylphosphine)dichloropalladium, or bis(triphenylphosphine)phenylpalladium iodide. Rhodium may be employed, for example, as the carbonyl complex. Nickel may be employed, for example, as nickel chloride or bis(triphenylphosphine)nickel chloride.

The above-described transition metal catalyst is employed in an amount in the range from 0.1 to 10 mol%, preferably from 1 to 5 mol% per mole of the iodonium salt.

The base is employed in the present employed for activating the transition metal catalyst as well as for neutraling the counter ion. Any of the bases that will not inhibit the reaction, that is, will not inactivate the transition metal catalyst by coordination with said catalyst and are soluble in the solvent used, are employed. For example, tertiary alkylamines, such as tripropylamine and tributylamine and alkali metal salts of lower fatty acids such as sodium acetate, potassium acetate, sodium formate and potassium formate are preferably employed. Alkali metal hydroxides such as sodium hydroxide and potassium hydroxide and alkali metal carbonates or bicarbonates such as sodium carbonate, potassium carbonate, sodium bicarbonate and potassium bicarbonate may also be used when the reaction solvent is water, an alcohol or a mixture thereof.

When carbon monoxide is an unsaturated compound for the addition reaction in the present invention, a reducing metal may be employed in place of the above-described base. As described above, the aryl compound produced in this case is a diaryl ketone or a diaryl diketone. As the metal may be employed any of the metals that can reduce the transition metal catalyst under the reaction conditions and neutralize the counter ion. For example, one metal or an alloy of two or more metals selected from the group consisting of zinc, copper, tin, mercury and silver. Metallic zinc, copper or their alloy is preferred because of a high yield produced.

Various polar solvents may be employed as the reaction solvent provided that the diaryl iodonium salt is partially soluble in it and it will not inhibit the reaction. For example, it may be appropriately selected from water, lower alcohols such as methanol and ethanol, ketones such as acetone and methylethylketone, ethers such as dimethoxyethane, tetrahydrofuran and dioxane as well as dimethylformamide (DMF), dimethylsulfoxide (DMSO), acetonitrile and the like.

The first-stage reaction of the present invention proceeds moderately and rapidly. As a matter of fact, the reaction pressure is usually atmospheric one, which is sufficient for the reaction to proceed, and to apply high pressure is unnecessary. If carbon monoxide or a low boiling unsaturated compound or solvent is used, the reaction may be conducted under pressure in order to prevent loss of the same. A reaction time in the range from about 0.1 to 10 hours is usually sufficient.

It is essential to operate the first-stage reaction under such conditions that no further reaction of the by-product iodoarene proceed and no substantial formation of a neutral iodine salt takes place, because such further reaction is possible.

To satisfy these conditions at least one component of base, reducing metal and unsaturated compound should not be used in excess.

In fact, the base or reducing metal used in the first-stage reaction is consumed as a result of the neutralization of the counter ion for the iodonium ion, and conversion of the iodoarene by-product requires the presence of a base. Therefore, use of a base in much excess of the amount sufficient neutralize the counter ion for the diaryl iodonium ion will cause conversion of the iodoarene due to the presence of a base in an excess amount. Usually, the base is employed in an amount not more than 1.5 times, and preferably from 0.8 to 1.2 times the stoichiometric amount per mole of the diaryl iodonium salt. Amount of the reducing metal is also in the same range.

In addition, no conversion of the iodoarene occurs also under such reaction conditions that no excess of the unsaturated compound is used. Because, as described above, an aryl compound such as iodobenzene is reacted with an unsaturated compound in the presence of a base and a transition metal catalyst with the result that the iodine in the iodoarene is converted to a neutral iodate salt according to the reaction by Heck et al. The unsaturated compound is employed usually in an amount not more than 1.5 times and preferably from about 0.8 to 1.2 times the stoichiometric amount per mole of the diaryl iodonium salt.

It is also appropriate to carry out the reaction at a temperature not higher than 80° C. and preferably not higher than 70° C. in order to inhibit the side reaction, namely, further reaction of the iodoarene.

If the first-stage reaction of the invention is carried out under the conditions as described above, not only the desired aryl compound is obtained but also the iodoarene by-product will not undergo further reaction thereby maximizing recovery of the iodine in the form of iodoarene.

After completion of the first-stage reaction, the desired aryl compound is separated by a separation process such as distillation or recrystallization. The iodoarene by-product is also separated by a similar process.

The second stage of the present invention involves coupling of the iodoarene thus separated with the aromatic compound Ar—H in an oxidizing atmosphere in the presence of $X^{\ominus}$ or an anion exchangeable with $X^{\ominus}$ to give the diaryl iodonium salt represented by the above-mentioned formula (I). The diaryl iodonium salt thus obtained, which is the starting material for the first-stage reaction, may be returned to the first-stage reaction thereby enabling recycling of expensive iodine with minimum loss of the same.

The aromatic compound to be coupled with an iodoarene in the second-stage reaction is an aromatic hydrocarbon Ar—H corresponding to the aryl group of a diaryl iodonium compound represented by the above-mentioned formula (I).

Therefore, it is an aromatic hydrocarbon of the condensed or uncondensed type in which the basic skeltone is benzene, indane, naphthalene or the like.

In particular, preferred example is benzene or a derivative thereof represented by the following formula:

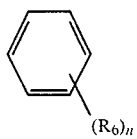

(V)

wherein $R_6$ is hydrogen atom, a $C_1$–$C_{12}$ alkyl group, a $C_6$–$C_{12}$ cycloalkyl such as cyclohexyl group, a lower aryl group, a lower halogenoalkyl group, a halogen atom, a carboxyl group, a lower alkoxycarbonyl group, a nitro group or a lower acylamino group, and n is an integer from 0 to 3 inclusive.

Illustrative are benzene, toluene, xylene, n-propylbenzene, isopropylbenzene, n-butylbenzene, t-butylbenzene, sec-butylbenzene, iso-butylbenzene, cyclohexylbenzene, biphenyl, trifluoromethylbenzene, chlorobenzene, bromobenzene, benzoic acid, phthalic acid, esters of these acids, anisole, nitrobenzene, N-acl anilides and the like.

In order to carry out the reaction in an oxidizing atmosphere an inorganic or organic oxidizing agent is usually used. A variety of oxidizing agents may be employed such as, for example, salts of persulfuric acid with alkali metals including potassium and sodium and the ammonium salt and alkali earth metal peroxides including barium peroxide. Preferred examples of the organic peroxide are peracids. As preferred examples of the peracid are mentioned perbenzoic acid and peracetic acid, which are readily available. Various peracids are also made available easily by combination of a carboxylic acid and hydrogen peroxide.

An oxidation process with no oxidizing agent needed, so-called electrolytic oxidation in which oxidation is electrically effected may be used.

An acid catalyst is used for effecting the coupling reaction. Sulfuric acid is a preferred acid catalyst. Concentration of the sulfuric acid used may be variable starting with concentrated sulfuric acid. When the substituent on aromatic hydrocarbons or the aryl group of iodoarene is an electron-attractive group, it is preferred to use sulfuric acid at a higher concentration. On the other hand, when it is an electron-donative group, use of a lower concentration allows the coupling reaction to proceed in a high yield.

In the second-stage coupling reaction of the present invention, solvents inert to the reaction may be employed. However, it is usually convenient to use as the solvent the concentrated sulfuric acid catalyst, the sulfuric acid or the fuming sulfuric acid catalyst diluted with a appropriate diluent. The diluent to be used for dilution of sulfuric acid or a fuming sulfuric acid may be any of the liquids that are substantially miscible with concentrated or fuming sulfuric acid and will not participate in the coupling reaction. Examples are water, fatty acids such as acetic acid, fatty acid anhydrides such as acetic anhydride and mixtures thereof.

Temperature of the coupling reaction is in the range between $-20°$ and $+30°$ C., preferably between $-10°$ and $+25°$ C. The reaction hardly proceeds at a temperature below $-20°$ C., and is associated with side reactions such as sulfonation with sulfuric acid at a temperature over $+35°$ C. The reaction time may appropriately be chosen and usually is in the range from one hour to several tens hours.

As described above, the coupling reaction affords a diaryl iodonium salt for which the counter ion is bisulfate ion $HSO_4^{\ominus}$ when sulfuric acid is the acid catalyst. The counter ion may be ion-exchanged with an appropriate anion. When the diaryl iodonium salt is employed again in the first-stage reaction of the invention, it is preferable to convert the anion to a halogenide ion as described above for the formula (I) because of easy separation and purification of the salt.

The conversion to a halogenide ion is easily carried out by ion-exchange with an inorganic halide that forms a halogenide ion. As the inorganic halide are mentioned alkali metal halide such as sodium chloride, potassium bromide and potassium iodide and ammonium halide salts such as ammonium chloride, ammonium bromide and ammonium iodide.

The process according to the present invention will be described in more details by means of examples.

EXAMPLE 1

The first-stage reaction was carried out by stirring a mixture of 361 g. (1 mole) of diphenyl iodonium bromide, 95 g. (1.1 mole) of methyl acrylate and 82 g. (1 mole) of sodium acetate in 1 l of methanol solvent together with 0.1 g. of palladium-on-active carbon catalyst at a temperature of 55° C. for a period of 4 hours. After completion of the reaction, the mixture was cooled to room temperature followed by separation of the catalyst by filtration. The methanol solvent was then removed by distillation and the reaction product was separated by distillation under reduced pressure. There were obtained 196 g. of a distillate (1) boiling at 65° C.–75° C. at 10 mmHg and 149 g. of a distillate (2) boiling at 125° C.–140° C.

The distillate (1) and the distillate (2) were found by infrared absorption analysis and nuclear magnetic resonance analysis to be iodobenzene (yield 96%) and methyl cinnamate (yield 92%), respectively. The yields are in terms of the molar yield on the basis of the charged diphenyl iodonium bromide.

The second-stage reaction was carried out by adding 164 g. of ammonium persulfate to a solution of 92 g. of the iodobenzene recovered as above and 70 g. of benzene in 74% by weight of aqueous sulfuric acid cooled to $-10°$ C. and stirring the resulting mixture for 20 hours. Then, to the mixture was added 500 g. of water followed by addition of a solution of 60 g. of potassium bromide in 400 g. of water. The resulting mixture was stirred for 30 min. to form precipitates which were separated by filtration, washed with water and dried. There were obtained 156 g. of powders which was identified by IR absorption analysis and NMR analysis to be diphenyl iodonium bromide.

These processes enabled to recycle iodine in a recovery ratio of 92% on the basis of the starting diphenyl iodonium bromide.

COMPARATIVE EXAMPLE 1

The first-stage reaction was carried out in the same way as in Example 1 except that 172 g. (2 mole) of methyl acrylate and 135 g. (1.6 mol) of sodium acetate were used and the reaction time was 7 hours. Yield of iodobenzene was reduced to 46%. Yield of the desired methyl cinnamate was over 130%. The iodine in the iodonium salt which was not recovered in the form of iodobenzene was almost converted to iodic acid or its salts.

Next, the first-stage reaction was carried out in the same way in Example 1 except that the reaction is conducted at 100° C. and under pressure. Yield of iodobenzene was reduced to 60%.

EXAMPLE 2

The first-stage reaction was carried out in the same way as in Example 1 except that 172 g. (2 mole) of methyl acrylate and 82 g. (1.0 mole) of sodium acetate were used. There were obtained 73 g. (0.85 mole) of unreacted methyl acrylate, 193 g. of iodobenzene and 151 g. of the desired methyl cinnamate. Yields of iodobenzene and methyl cinnamate were 95% and 93%, respectively.

Next, the first-stage reaction was carried out in the same way as in Example 1 using 95 g. (1.1 mole) of methyl acrylate and 164 g. (2 mole) of sodium acetate. There were obtained 177 g. of iodobenzene and 170 g. of the desired methyl cinnamate. Yields of iodobenzene and methyl cinnamate were 87% and 105%, respectively.

It is seen from Examples 1 and 2 and Comparative Example 1 that iodobenzene and methyl cinnamate can be obtained simultaneously in good yields by meeting at least one requirement, that (1) the base is not used excessively (2) the unsaturated compound is not used excessively and (3) the reaction temperature does not exceed 80° C.

EXAMPLE 3

The reaction was carried out in the same way using diaryl iodonium salts and unsaturated compounds indicated in Table 1, and the iodoarenes thus obtained were coupled with aromatic hydrocarbons at a sulfuric-acid concentration shown in Table 2 to recover the diaryl iodonium salts. Recovery ratios of iodine were also shown in Table 2.

TABLE 2

| No. | Iodoarene | Aromatic hydrocarbon | (Concentration of H$_2$SO$_4$.) wt % Solvent | Reaction Condition | Recovery Ratio of iodine (%) |
|---|---|---|---|---|---|
| 1 | p-Iodobenzene | Benzene | (75) H$_2$O | −5° C. 20 hrs. | 91 |
| 2 | p-Iodo heptyl benzene | Heptyl benzene | (80) CH$_3$COOH | −5° C. 20 hrs. | 88 |
| 3 | p-Iodo cyclohexyl benzene | Cyclohexyl benzene | (75) H$_2$O | −5° C. 20 hrs. | 89 |
| 4 | p-Iodo biphenyl | Biphenyl | (70) CH$_3$COOH | 0° C. 15 hrs. | 79 |
| 5 | p-Iodo trifluoromethyl benzene | Trifluoromethyl benzene | (85) H$_2$O | 0° C. 15 hrs. | 84 |
| 6 | p-Iodo bromobenzene | Bromobenzene | (40) CH$_3$COOH | 10° C. 15 hrs. | 88 |
| 7 | Methyl-p-iodo benzoate | Methyl benzoate | (70) CH$_3$COOH | 0° C. 20 hrs. | 67 |
| 8 | p-Iodo anisole | Anisole | (5) CH$_3$COOH | 20° C. 30 hrs. | 74 |
| 9 | Iodo benzene | Benzene | (75) H$_2$O | −5° C. 20 hrs. | 90 |
| 10 | Iodo benzene | Benzene | (75) H$_2$O | −5° C. 20 hrs. | 88 |
| 11 | Iodo benzene | Benzene | (75) H$_2$O | −5° C. 20 hrs. | 90 |

EXAMPLE 4

The first-stage reaction was carried out by stirring a mixture of 361 g. (1 mole) of diphenyl iodonium bromide, 115 g. (1.1 mole) of styrene and 185 g. (1 mole) of the base (n-Bu)$_3$N in 1 l of methyl alcohol together with 0.1 g. of bis(benzylideneacetone)palladium (Pd(dba)$_2$) catalyst at a temperature of 50° C. for a period of 6 hours. After completion of the reaction, the mixture was cooled to room temperature followed by separation of the catalyst by filtration. The methyl alcohol was removed by distillation, and the residue was subjected

TABLE 1

| No. | Iodonium Salt (moles) | Unsaturated Compound (moles) | Aryl Compound (% Yield) | Iodoarene (% Yield) |
|---|---|---|---|---|
| 1 | Diphenyl iodonium bromide (1.0) | Methyl methacrylate (1.05) | Methyl α-methylcinnamate (94) | Iodo benzene (96) |
| 2 | Bis(p-heptylphenyl)iodonium bromide (1.0) | Methyl acrylate (1.1) | Methyl p-heptylcinnamate (92) | p-iodo heptyl benzene (95) |
| 3 | Bis(cyclohexylphenyl)iodonium bromide (1.0) | Methyl acrylate (1.1) | Methyl p-cyclocinnamate (93) | p-iodo cyclohexyl benzene (96) |
| 4 | Di(p-biphenylyl)iodonium bromide (1.0) | Methyl acrylate (1.1) | Methyl p-biphenylcinnamate (91) | p-iodo biphenyl (92) |
| 5 | Bis(p-trifluoromethylphenyl)- iodonium brimide (1.0) | Methyl acrylate (1.1) | Methyl p-trifluoromethyl-cinnamate (87) | p-iodo trifluoromethyl-benzene (90) |
| 6 | Bis(p-bromophenyl)iodonium bromide (1.0) | Methyl acrylate (1.1) | Methyl p-bromocinnamate (94) | p-iodo bromo-benzene (97) |
| 7 | Bis(p-methoxycarbonylphenyl)- iodonium bromide (1.0) | Methyl acrylate (1.1) | Methyl p-methoxycarbonyl-cinnamate (97) | Methyl-p-iodo-benzoate (97) |
| 8 | Bis(p-methoxyphenyl)iodonium bromide (1.0) | Methyl acrylate (1.1) | Methyl p-methoxycinnamate (96) | p-iodo anisole (94) |
| 9 | Diphenyl iodoniium bromide (1.0) | Methyl vinyl ketone (1.1) | Benzylidene acetone (94) | Iodo benzene (95) |
| 10 | Diphenyl iodonium bromide (1.0) | Acrolein (1.1) | p-Formyl styrene (89) | Iodo benzene (91) |
| 11 | Diphenyl iodonium bromide (1.0) | Maleic anhydride (1.1) | Phenylmaleic anhydride (87) | Iodo benzene (94) | to distillation under reduced pressure to give 192 g. of a distillate (1) boiling at 65°–75° C. at 10 mmHg and then steam distillation to recover 171 g. of a distillate (2).

IR spectra and NMR spectra indicated that the distillate (1) was iodobenzene (yield 94%) and the distillate (2) was the desired product, stilbene (trans form) (yield 95%).

Then, the second-stage reaction was carried out in the same way as in the second-stage reaction of Example 1 using 92 g. of iodobenzene and 100 g. of benzene for the coupling reaction and the ion exchange with potassium bromide. There was obtained 158 g. of powdery diphenyl iodonium bromide. Yield in terms of the iodonium salt was 97%.

Recovery ratio in terms of iodine was 91%.

EXAMPLE 5

Diaryl iodonium salts and unsaturated compounds shown in Table 3 were reacted followed by coupling of the iodoarenes thus obtained with aromatic hydrocarbons under the conditions shown in Table 4. Recovery ratio of iodine are shown in Table 4.

The experiment No. 13 in which isobutylene was employed was conducted under pressure in order to avoid loss of the isobutylene.

hol all at once. The resulting mixture was reacted for 2 hours.

There were produced cyclamen aldehyde in a yield of 88% and p-iodo-cumene in a yield of 98%.

Also, lily aldehyde was obtained in a yield of 88% and p-iodo-t-butylbenzene in a yield of 95%.

These iodoarenes were then coupled respectively with cumene and t-butylbenzene in the same way as in Example 1 to give the same iodonium salts as the starting iodonium salts. Recovery ratio of iodine were 93% and 90%, respectively.

EXAMPLE 7

An ordinary pressure-reduction apparatus equipped with a gas burette was used as the reaction apparatus. In the apparatus were placed 361 g. (1 mole) of diphenyl iodonium bromide, 0.3 g. of $PdCl_2$ catalyst, 185 g. (1 mole) of $(n-Bu)_3N$ base and 1 l of methyl alcohol. The system was purged 3–4 times with carbon monoxide. Then, the mixture was stirred at room temperature. Absorption of carbon monoxide as estimated by reduction in amount of the gas filled in the burette was 1.05 moles.

After completion of the reaction, the catalyst was separated by filtration. The methyl alcohol was re-

TABLE 3

| No. | Iodonium Salt (moles) | Unsaturated Compound (moles) | Aryl Compound (%, Yield) | Iodoarene (% Yield) |
|---|---|---|---|---|
| 12 | Diphenyl iodonium bromide (1.0) | α-Methyl styrene (1.05) | α-Methyl stilbene (35) | Iodo benzene (97) |
| 13 | Diphenyl iodonium bromide (1.0) | Isobutylene (1.1) | 1-Phenyl-2-methyl propene (65) | Iodo benzene (96) |
| 14 | Bis(p-heptylphenyl)iodonium bromide (1.0) | Styrene (1.1) | p-Heptyl stilbene (91) | p-Iodo heptylbenzene (95) |
| 15 | Bis(p-methoxycarbonylphenyl) iodonium bromide (1.0) | Styrene (1.1) | p-Methoxycarbonyl stilbene (91) | Methyl-p-iodo-benzoate (90) |
| 16 | Bis(p-methoxyphenyl)iodonium bromide (1.0) | Styrene (1.1) | p-Methoxy stilbene (93) | p-Iodo anisole (97) |
| 17 | Bis(p-succinimidophenyl) iodonium bromide (1.0) | Styrene (1.1) | p-Succinimido stilbene | N—(p-iodophenyl)-succinimide (90) |
| 18 | Bis(m-nitrophenyl)iodonium bromide (1.0) | Styrene (1.1) | m-Nitro stilbene (85) | m-Nitro iodo-benzene (88) |

TABLE 4

| No. | Iodoarene | Aromatic hydrocarbon | (Concentration of $H_2SO_4$, wt %) Solvent | Reaction condition | Recovery ratio of iodine (%) |
|---|---|---|---|---|---|
| 12 | Iodo benzene | Benzene | (75) $H_2O$ | −15° C. 20 hrs. | 92 |
| 13 | Iodo benzene | Benzene | (75) $H_2O$ | −15° C. 20 hrs. | 91 |
| 14 | p-Iodo heptylbenzene | Heptylbenzene | (80) $CH_3COOH$ | −15° C. 20 hrs. | 88 |
| 15 | Methyl-p-iodo benzoate | Methyl benzoate | (70) $CH_3COOH$ | 0° C. 20 hrs. | 62 |
| 16 | p-Iodo anisole | Anisole | (5) $CH_3COOH$ | 20° C. 30 hrs. | 76 |
| 17 | N—(p-iodophenyl)-succinimide | N—phenylsuccinimide | (10) $CH_3COOH$ | 15° C. 30 hrs. | 63 |
| 18 | m-Nitro iodo benzene | Nitrobenzene | (83) $H_2O$ | −5° C. 15 hrs. | 66 |

EXAMPLE 6

In a three-necked flask were placed methanol (100 ml.), potassium acetate as a base (100 mmol.) and a diaryl iodonium salt (100 mmol.) which is is bis(p-isopropylphenyl)iodonium bromide or bis(p-t-butylphenyl)iodonium bromide. The flask was purged with nitrogen followed by addition of Pd black (5 mmol.). To the mixture heated to 50° C. was added methallyl alcomoved by distillation, and the reside was subjected to distillation under reduced pressure to recover 189 g. of a distillate (1) boiling at 65°–75° C. at 10 mmHg and 133 g. of a distillate (2) boiling at 80°–90° C.

IR spectra and NMR spectra indicated that the distillate was iodobenzene (yield 93%) and the distillate (2) was the desire product, methyl benzoate (yield 98%).

Then, the second-stage reaction was carried out in the same way as in the second-stage reaction of Example 1 using 92 g. of the recovered iodobenzene and 150 g. of benzene for the coupling reaction and the ion exchange with potassium bromide. There was obtained 160 g. of powdery diphenyl iodonium bromide. Yield as the iodonium salt was 98%. Recovery ratio as iodine was 91%.

EXAMPLE 8

Diaryl iodonium salts shown in Table 5 were reacted with carbon monoxide in the same way as in Example 7. The iodoarenes thus formed were then coupled with aromatic hydrocarbons under the conditions shown in Table 6 to recover the same diaryl iodonium salts as the starting ones. Recovery ratios of iodine were also shown in Table 6.

carbon monoxide absorption. Absorption of carbon monoxide was ceased in 30 min.–60 min., and stirring was continued for additional 30 min. to complete the reaction. After removal of the catalyst, the product was separated by distillation and identified by gas chromatography, IR and NMR. The yield was determined on the basis of gas chromatography.

Results are shown in Table 7. The yield in the table is expressed in molar percent per mole of the diaryl iodonium salt. In the reactions Nos. 1–16 in the table there were by-produced, in addition to the products in the table, iodobenzene for the iodonium A, p-iodotoluene for the iodonium salt B and p-iodo-t-butylbenzene for the iodonium salt C yields in the range from 93% to 100%.

Subsequently, iodobenzene, p-iodotoluene and iodo-t-butylbenzene were coupled respectively with ben-

TABLE 5

| No. | Iodonium Salt (moles) | Aryl Compound (% Yield) | Iodoarene (% Yield) |
|---|---|---|---|
| 19 | Bis(p-heptylphenyl)iodonium bromide (1.0) | Methyl-p-heptyl benzoate (98) | p-Iodo heptyl benzene (97) |
| 20 | Bis(p-methoxycarbonylphenyl) iodonium bromide (1.0) | Dimethyl terephthalate (100) | Methyl-p-iodo benzoate (96) |
| 21 | Bis(p-ethoxyphenyl)iodonium bromide (1.0) | Methyl-p-ethoxy benzoate (101) | p-Iodo phenetole (96) |

TABLE 6

| No. | Iodoarene | Aromatic hydrocarbon | (Concentration of $H_2SO_4$, wt %) Solvent | Reaction Condition | Recovery ratio of iodine % |
|---|---|---|---|---|---|
| 19 | p-Iodo heptyl benzoate | Heptyl benzene | (80) $CH_3COOH$ | −5° C. 20 hrs. | 90 |
| 20 | Methyl-p-iodo benzoate | Methyl benzoate | (70) $CH_3COOH$ | 20° C. 30 hrs. | 66 |
| 21 | p-Iodo phenetole | Phenetole | (5) $CH_3COOH$ | 20° C. 30 hrs. | 76 |

EXAMPLE 9

In a flask were placed a solvent (10 ml.), a palladium acetate catalyst (0.1 mmol.), a diaryl iodonium salt (2 mmol.) and metal powders (2 mmol.) shown in Table 7, and the flask was filled with carbon monoxide and subjected to stirring at room temperature to completion of zene, toluene and t-butylbenzene in the same way as in the second-stage reaction of Example 1 to give the same iodonium salts as the starting iodonium salts respectively in yields in the range from 92% to 96%. Recovery ratios of iodine were in the range from 74% to 82%.

TABLE 7

| No. | Iodonium Salt | Counter Ion | Solvent | Metal | Ketone (% yield) | | Diketone (% yield) | |
|---|---|---|---|---|---|---|---|---|
| 1 | A | Cl | Acetone | Zn | Benzophenone | 56 | Benzil | 24 |
| 2 | " | " | DMF | " | " | 58 | Benzil | 25 |
| 3 | " | " | DMF | " | " | 55 | Benzil | 8 |
| 4 | " | Br | $CH_3CN$ | " | " | 12 | Benzil | 8 |
| 5 | " | I | Acetone | " | " | 60 | Benzil | 11 |
| 6 | " | $BF_4$ | " | " | " | 48 | Benzil | 21 |
| 7 | " | Cl | " | " | " | 42 | Benzil | 15 |
| 8 | " | " | " | Cu | " | 31 | Benzil | 17 |
| 9 | " | " | " | Zn—Cu | " | 34 | Benzil | 10 |
| 10(1) | " | " | " | Zn | " | 61 | Benzil | 23 |
| 11(2) | " | " | " | " | " | 36 | Benzil | 3 |
| 12(3) | " | " | " | " | " | 60 | Benzil | 15 |
| 13(4) | " | " | " | " | " | 60 | Benzil | 21 |
| 14(5) | " | " | " | " | " | 59 | Benzil | 23 |
| 15 | B | Br | " | " | 4,4'-Dimethylbenzophenone | 61 | 4,4'-Dimethylbenzil | 18 |
| 16 | C | " | " | " | 4,4'-Di(t-butyl)- | 47 | 4,4'-Di(t- | 8 |

TABLE 7-continued

| No. | Iodonium Salt | Counter Ion | Solvent | Metal | Ketone (% yield) | Diketone (% yield) |
|---|---|---|---|---|---|---|
| | | | | | benzophenone | butyl)benzil |

A: Diphenyl iodonium salt
B: Ditolyl iodonium salt
C: Bis(t-butylphenyl)iodonium salt
(1) Reaction temperature 5° C.
(2) Reaction temperature 50° C.
(3) Zn 4 mmol.
(4) Zn 1.0 mmol.
(5) Catalyst PdCl₂

COMPARATIVE EXAMPLE 2

The first-stage reaction was carried out in the same way as No. 1 experiment of the Example 9 except that 6 mmol. of metal powder was used and the reaction time was 3 hours. Yield of iodobenzene was reduced to 51%.

Next, the first-stage reaction was carried out in the same way as No. 1 experiment of the Example 9 except that reaction temperature was 85° C. Yield of iodobenzene was reduced to 48%.

What is claimed is:

1. A process for converting an aromatic compound to prepare an iodoarene, Ar—I, and an aryl compound which is a compound wherein an unsaturated compound is bonded directly to an aryl group, Ar, which process comprises reacting a diaryliodonium salt represented by general formula (I)

[Ar—I⊕—Ar]X⊖    (I)

wherein Ar is an aryl group which may be substituted and two Ar's are identical and X⊖ is a counter ion inert to the reaction with the unsaturated compound in a solvent in the presence of a transition metal catalyst and a base or a reducing metal, said reaction being carried out at a temperature not higher than 80° C. and/or by using at least one of the base, the reducing metal and the unsaturated compound in an amount not more than 1.5 times the stoichiometric amount, then separating the iodoarene thus formed, Ar—I, from the reaction mixture, subsequently coupling said iodoarene thus separated with an aromatic compound, ArH, in an oxidizing atmosphere in the presence of X⊖ or an anion ion-exchangeable with X⊖, if needed ion-exchanging the anion with X⊖, to form the diaryl iodonium salt of the above general formula (I), and recycling said diaryl iodonium salt thus formed in said reaction.

2. The process according to claim 1 wherein the transition metal catalyst is a palladium catalyst.

3. The process according to claim 1 wherein the unsaturated compound is a compound containing an olefinic double bond.

4. The process according to claim 3 wherein the olefinic double bond-containing compound is selected from the group consisting of styrenes, aliphatic olefins and α,β-unsaturated carbonyl compounds.

5. The process according to claim 4 wherein the α,β-unsaturated carbonyl compound is an α,β-unsaturated mono- or di-carboxylic acid, ester or anhydride thereof.

6. The process according to claim 4 wherein the α,β-unsaturated carbonyl compound is an α,β-unsaturated aldehyde or an α,β-unsaturated ketone.

7. The process according to claim 1 wherein the unsaturated compound is carbon monoxide.

8. The process according to claim 1 wherein the reducing metal is one metal or alloy of two or more metals selected from the group consisting of zinc, copper, tin, mercury, and silver.

* * * * *